US011538163B1

(12) United States Patent
Li et al.

(10) Patent No.: US 11,538,163 B1
(45) Date of Patent: Dec. 27, 2022

(54) TRAINING A NEURAL NETWORK FOR A PREDICTIVE AORTIC ANEURYSM DETECTION SYSTEM

(71) Applicant: Rowan University

(72) Inventors: Yupeng Li, Blackwood, NJ (US); Hieu Duc Nguyen, Turnersville, NJ (US); Shao Tang, Cupertino, CA (US)

(73) Assignee: ROWAN UNIVERSITY, Glassboro, NJ (US)

( * ) Notice: Subject to any disclaimer, the term of this patent is extended or adjusted under 35 U.S.C. 154(b) by 0 days.

(21) Appl. No.: 17/682,407

(22) Filed: Feb. 28, 2022

Related U.S. Application Data

(60) Provisional application No. 63/296,993, filed on Jan. 6, 2022.

(51) Int. Cl.
G06T 7/00 (2017.01)
G06V 10/22 (2022.01)
(Continued)

(52) U.S. Cl.
CPC ............ *G06T 7/0016* (2013.01); *A61B 6/466* (2013.01); *A61B 6/504* (2013.01); *A61B 6/5217* (2013.01);
(Continued)

(58) Field of Classification Search
CPC ......... G06T 7/0016; G06T 3/40; G06T 5/007; G06T 5/50; G06T 7/11; G06T 7/60;
(Continued)

(56) References Cited

U.S. PATENT DOCUMENTS 6,016,384 A * 1/2000 Gallo ................... G06K 9/6255
706/16
2003/0187688 A1* 10/2003 Fey ........................ G16H 10/60
705/2
(Continued)

FOREIGN PATENT DOCUMENTS

CN 110264449 A 9/2019
CN 112309574 A 2/2021
(Continued)

OTHER PUBLICATIONS

Lopez-Linares et al., "Fully automatic detection and segmentation of abdominal aortic thrombus in post operative CTA images using deep convolutional networks," Medical image analysis 46 (2018): 202-214. Apr. 1, 2018, retrieved on Apr. 22, 2022 from <https://arxiv.org/pdf/1804.00304.pdf> (Year: 2018).*
(Continued)

*Primary Examiner* — Van D Huynh
(74) *Attorney, Agent, or Firm* — FisherBroyles, LLP

(57) ABSTRACT

Systems and methods for detecting aortic aneurysms using ensemble based deep learning techniques that utilize numerous computed tomography (CT) scans collected from numerous de-identified patients in a database. The system includes software that automates the analysis of a series of CT scans as input (in DICOM file format) and provides output in two dimensions: (1) ranking CT scans by risks of adverse events from aortic aneurysm, (2) providing aortic aneurysm size estimates. A repository of CT scans may be used for training of deep neural networks and additional data may be drawn from localized patient information from institutions and hospitals which grant permission.

20 Claims, 9 Drawing Sheets

(51) Int. Cl.
| | |
|---|---|
| *G06T 17/00* | (2006.01) |
| *G06K 9/62* | (2022.01) |
| *G06V 10/82* | (2022.01) |
| *G06T 5/50* | (2006.01) |
| *G06T 7/60* | (2017.01) |
| *G06T 7/11* | (2017.01) |
| *G06T 3/40* | (2006.01) |
| *G16H 30/40* | (2018.01) |
| *G16H 50/20* | (2018.01) |
| *A61B 6/00* | (2006.01) |
| *G06T 5/00* | (2006.01) |
| *A61B 6/03* | (2006.01) |

(52) U.S. Cl.
CPC .............. *G06K 9/6257* (2013.01); *G06T 3/40* (2013.01); *G06T 5/007* (2013.01); *G06T 5/50* (2013.01); *G06T 7/11* (2017.01); *G06T 7/60* (2013.01); *G06T 17/00* (2013.01); *G06V 10/225* (2022.01); *G06V 10/82* (2022.01); *G16H 30/40* (2018.01); *G16H 50/20* (2018.01); *A61B 6/032* (2013.01); *G06T 2207/10081* (2013.01); *G06T 2207/20081* (2013.01); *G06T 2207/20084* (2013.01); *G06T 2207/30048* (2013.01); *G06V 2201/031* (2022.01)

(58) Field of Classification Search
CPC ........... G06T 17/00; G06T 2207/10081; G06T 2207/20081; G06T 2207/20084; G06T 2207/30048; A61B 6/466; A61B 6/504; A61B 6/5217; A61B 6/032; G06K 9/6257; G06V 10/225; G06V 10/82; G06V 2201/031; G16H 30/40; G16H 50/20
USPC ....................................................... 345/419
See application file for complete search history.

(56) References Cited

U.S. PATENT DOCUMENTS

| | | | | |
|---|---|---|---|---|
| 2004/0054280 | A1* | 3/2004 | McMorrow | G06T 17/00 600/437 |
| 2008/0033302 | A1* | 2/2008 | Grady | G06T 7/0012 600/481 |
| 2008/0170763 | A1* | 7/2008 | Begelman | A61B 5/02007 382/128 |
| 2008/0181479 | A1* | 7/2008 | Yang | A61B 8/08 600/443 |
| 2009/0279758 | A1* | 11/2009 | Dikici | G06T 7/11 382/128 |
| 2010/0074494 | A1* | 3/2010 | Karmonik | G06T 7/12 382/131 |
| 2015/0086093 | A1 | 3/2015 | Fonte | |
| 2015/0203916 | A1 | 7/2015 | Ikonomidis | |
| 2019/0087957 | A1* | 3/2019 | Burris | A61B 5/0044 |
| 2019/0105008 | A1* | 4/2019 | Dehghan Marvast | A61B 6/507 |
| 2019/0156947 | A1* | 5/2019 | Nakamura | G16H 50/20 |
| 2019/0320992 | A1 | 10/2019 | Koyakumaru | |
| 2020/0160527 | A1* | 5/2020 | Rapaka | G06T 7/62 |
| 2020/0402232 | A1 | 12/2020 | Schoenhagen | |
| 2021/0128099 | A1 | 5/2021 | Al-Noor | |

FOREIGN PATENT DOCUMENTS

| | | |
|---|---|---|
| CN | 113223704 A | 8/2021 |
| EP | 3319552 B1 | 8/2021 |
| WO | 2020210278 A1 | 10/2020 |

OTHER PUBLICATIONS

International Search Report dated May 11, 2022, in International Application No. PCT/US2022/018162.
Written Opinion of the International Searching Authority dated May 11, 2022, in International Application No. PCT/US2022/018162.
Lopez-Linares et al., "Fully automatic detection and segmentation of abdominal aortic thrombus in post-operative CTA images using deep convolutional networks," Medical image analysis 46 (2018): 202-214. Apr. 1, 2018, retrieved on Apr. 22, 2022 from <https://arxiv.org/pdf/1804.00304.pdf>.
Wu et al., "Ascending aortic length and risk of aortic adverse events: the neglected dimension." Journal of the American College of Cardiology 74.15 (2018): 1883-1894/ Oct. 15, 2019, retrieved on Apr. 22, 2022 from <https://sciencedirect.com/science/article/pii/S0735109719362928>.
Jiang et al., "A deep learning approach to predict abdominal aortic aneurysm expansion using longitudinal data," Frontiers in Physics, vol. 7, Article 235, Jan. 15, 2020, pp. 1-13.

* cited by examiner

TRAINING A NEURAL NETWORK FOR A PREDICTIVE AORTIC ANEURYSM DETECTION SYSTEM

PRIORITY CLAIM

This application claims the benefit of U.S. Provisional Application No. 63/296,993, entitled "TRAINING A NEURAL NETWORK FOR A PREDICTIVE AORTIC ANEURYSM DETECTION SYSTEM," filed Jan. 6, 2022, which is incorporated by reference in its entirety herein for all purposes.

BACKGROUND

Healthcare, in general, has become increasingly digitized whereupon large volumes of clinical data is now generated on human patients at nearly every medical facility for many types of healthcare interactions. As the volume of data has increased, the complexity of retrieving, interpreting, and drawing useful conclusions from such collected data points has become even more challenging. This challenge is caused, in part, from the variability of the amount and type of clinical context available from data for a given patient under the backdrop of similar data collected for collective patients, at large.

The digitization of healthcare data has provided many opportunities for computer-based systems, including computer-assisted detection and clinical decision support systems, which can help clinicians work more efficiently. Advances in machine learning, artificial intelligence, and computer hardware have also enabled the development of efficient algorithms and models that can efficiently process and learn patterns from massive quantities of unstructured imaging data. However, the accuracy of such algorithms and models is often limited based on correct deployment and usage, which is likewise complicated by the variability of the amount and type of clinical context available from data for a given patient. Limited approaches and workflows have been utilized to customize the base of medical information for a given patient and define types of actions and outputs that can be taken when certain conditions are detected. However, such approaches are often implemented with individuality and manual analysis which then have limited applicability to the specific individual without benefit of collective analysis.

BRIEF DESCRIPTION OF THE DRAWINGS

The subject matter presented herein will now be described, by way of example, with reference to the accompanying drawings, in which.

DETAILED DESCRIPTION

Figure 1:
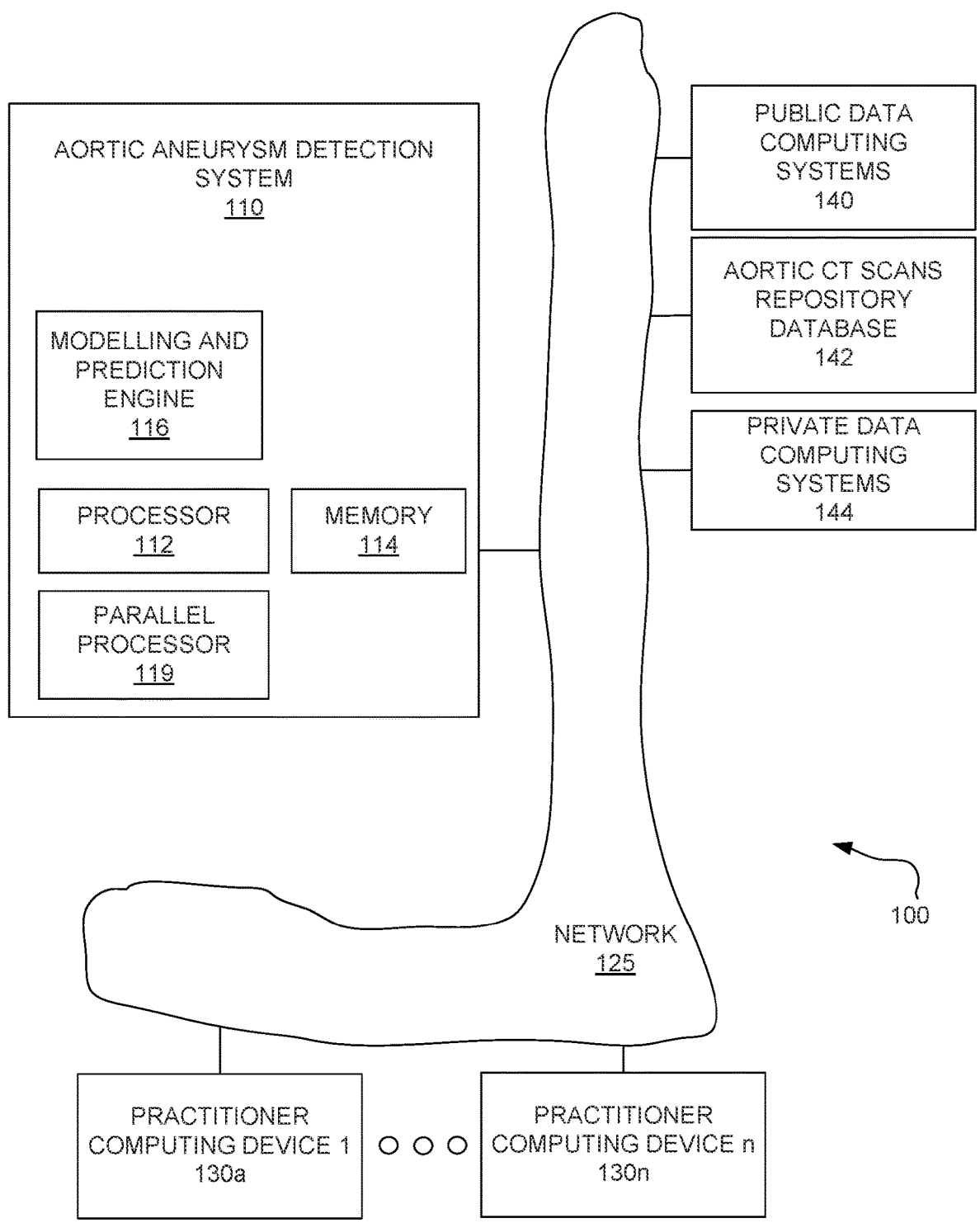
FIG. 1 is a block diagram of a computing environment for realizing the systems and methods of a predictive aortic aneurysm detection system and method according to an embodiment of the subject matter disclosed herein.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. Furthermore, there is no intention to be bound by any expressed or implied theory presented in the preceding technical field, background, brief summary of the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" as required by 35 U.S.C. § 112.

Byway of an overview, systems and methods for detecting aortic aneurysms using a deep learning neural network that utilizes numerous computed tomography (CT) scans collected from numerous anonymous patients in a database or data repository. A CT scan (formerly known as and sometimes still called a computed axial tomography or CAT scan) is a medical imaging technique used in radiology to obtain detailed internal images of the body noninvasively for diagnostic purposes. Individuals that perform CT scans are radiographers or radiology technologists and, as such, this disclosure and system is targeted for radiologists and vascular surgeons to improve the efficiency of detecting and prioritizing patients with high risk of aortic aneurysms. The system includes software that automates the analysis of a series of CT scans as input (in DICOM file format, as defined below) and provides output in two dimensions: (1) ranking CT scans by risks of aortic aneurysm, (2) providing aortic aneurysm size estimates. The algorithm relies on a deep-learning approach so that radiologists and vascular surgeons have a brief idea of which patients are at higher risk and therefore need higher priority to conduct further CT scan readings and possible surgery schedules on sight. In one embodiment, the repository of CT scans used for deep learning and neural network training is sourced from TCGA-LUAD, a publicly available database that provides CT scans for researchers. In further embodiments, additional data may be drawn from localized patient information from institutions and hospitals which grant permission (e.g., Cooper Hospital and the like).

The system disclosed herein is advantageous because a parallel processing pipeline is utilized that automates the analysis of CT scans to determine images slices that provide the most accurate detection and segmentation of aortic aneurysms. Moreover, the novel deep learning model combines three existing architectures, namely an ensemble objection detection model using both YOLO and Faster RCNN to detect the location of an aneurysm and a segmentation model using U-Net to calculate the size of the aneurysm. Experimental results show that the ensemble objection detection model is superior to each model separately. This system will help radiologists and vascular surgeons to detect and rank aortic aneurysm risks upfront, once CT scans are available.

In this manner, doctors will be notified on the risk priorities of patients beforehand and allow them to strategically do scan reading and diagnosis, and therefore greatly improve the efficiency of the diagnostic process. Further yet, the automatic feature of the subject matter system herein is expected to save 50% of radiologists' and vascular surgeons' time on CT scan readings. Additionally, the risk ranking system can provide real-time updates to all relevant doctors to strategically allocate their time schedule for patients. Lastly, the resultant early detection and in-time treatment for aortic aneurysm patients will yield much lower adverse event (mortality) rates.

These and other aspects may be more readily understood and further detailed with respect to the detailed description below with reference to FIGS. 1-12.

Turning attention to the figures, FIG. 1 is a block diagram of a computing environment 100 (e.g., an aortic aneurysm detecting system 100) for realizing the systems and methods of a predictive aortic aneurysm detection system according to an embodiment of the subject matter disclosed herein. The overall computing environment 100 may be generally comprised of three sets of computing devices that are all communicatively coupled to each other through a computing network 125, such as the Internet, though the network 125 may be a local Intranet or a virtual private network or the like. The three generalized categories of the coupled computers include an aortic aneurysm detection system 110, one or more medical professional computing-devices 1309-130n, and one or more data-service computing devices, such as public data collection devices 140, private data collection devices 144, and CT scan repository devices 142 (e.g., The Cancer Genome Atlas Lung Adenocarcinoma (TCGA-LUAD) repository). Other data-collection and/or data provision services (are contemplated but not shown in this figure here for brevity. The aortic aneurysm detection system 110, includes one or more local processors 112 including a parallel processing unit 119 (e.g., consisting of a central processing unit or CPU and a graphics processing unit or GPU) that utilizes one or more memories 114 in conjunction with an aortic aneurysm detection modelling and prediction engine 116.

A skilled artisan understands that this arrangement of computing devices may be subject to many permutations, inclusions and deletions, and the basic functionality described next may be carried out using multiple computing configurations within the context of FIG. 1. In specific, aspects of the operation and utilization of the aortic aneurysm detection system 110 are described next with respect to FIG. 2.

Figure 2:
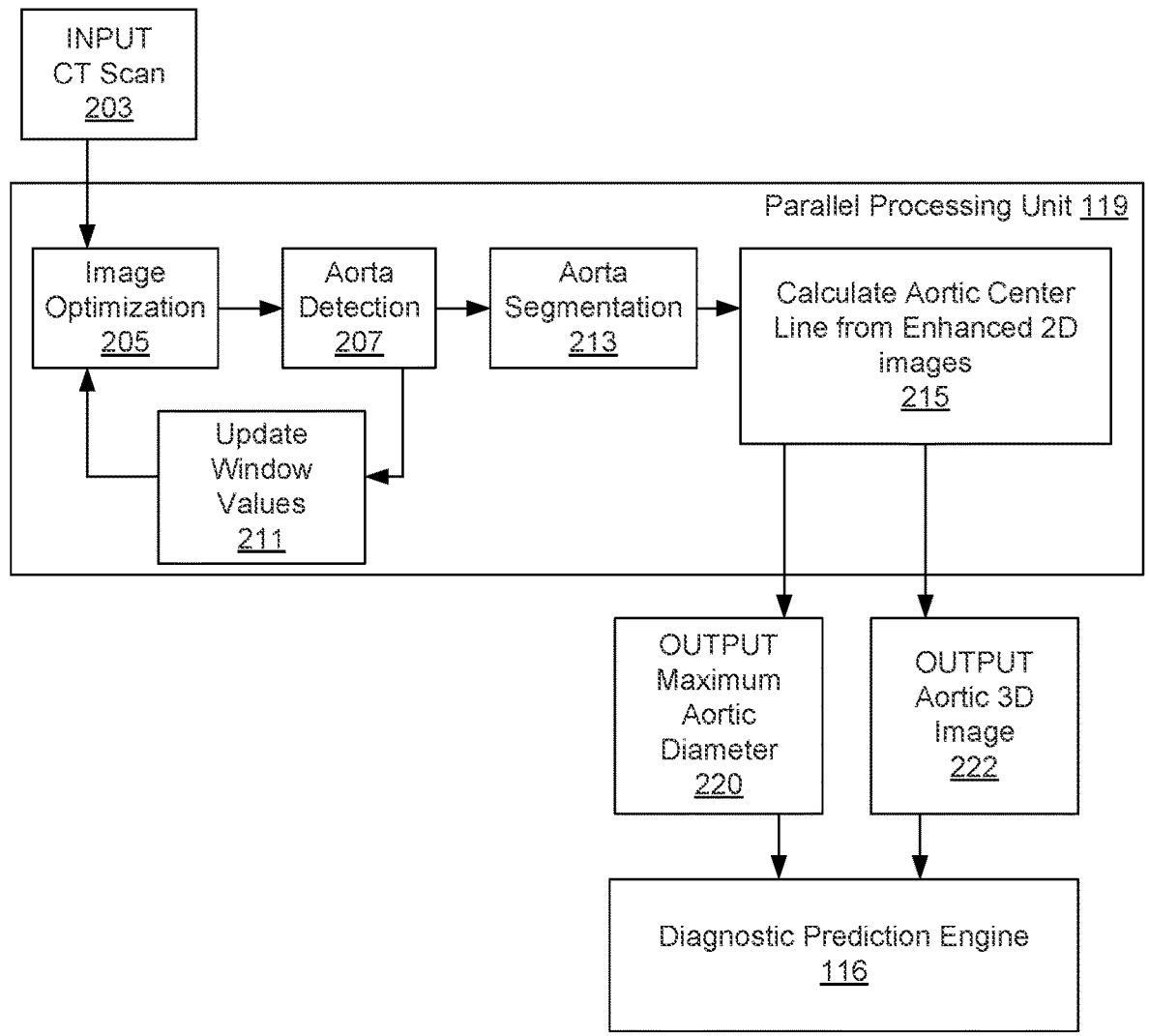
FIG. 2 is a more in-depth block diagram of an aortic aneurysm detection system of FIG. 1 according to an embodiment of the subject matter disclosed herein.

FIG. 2 is a more in-depth block diagram of the aortic aneurysm detection system 110 of the computing environment of FIG. 1 according to an embodiment of the subject matter disclosed herein. As shown in FIG. 2, the aortic aneurysm detection system 110 is shown with numerous logical computing blocks, sub-engines, and databases. The specific nature of these components is understood by a skilled artisan to be realized in physical form in known manners such programmable gate array logic, application-specific integrated circuits, neural networks, volatile memory systems and programmatic software-based or hardware-based executable instructions under the direction of one or more local or remote processors (not shown in FIG. 2). As such, the functionality of each sub-system is discussed without regard to specific realization as a skilled artisan understands numerous ways to realize the novel functionality described herein. Further, for ease of illustration several components of the system 100 of FIG. 1 are shown below the aortic aneurysm detection system 110 for facilitating this detailed description even though these components may be remote and under management of other processors and/or organizations.

In a first area of functionality, the aortic aneurysm detection system 110 includes a computing pipeline for inputting 203 previously collected and/or legacy Computed Tomography (CT) scans of aortic regions for modelling and training purposes as well as inputting new CT scan of current patients for predictions and diagnostics. IN this embodiment the computing pipeline may be accomplished using a parallel processing unit 119 (e.g., consisting of both a CPU and GPU). For each patient, the input data 203 may be a series of hundreds of 2-dimensional (2D) Digital Imaging and Communications in Medicine (DICOM) images processed from CT scans of the body (thoracic, abdominal) region. Some of these CT scans are shown below as ascending or descending aortic aneurysms as represented in FIGS. 6-10 below. The goals of the parallel processing pipeline 119 are to optimize the imagery from the inputted images and then determine maximum aorta sizes for ascending and descending sections of these scans as well as utilizing the measurements to perform one or more diagnoses of aortic aneurysms and optimal triaging for treatments. Aspects of the parallel processing pipeline 119 are described next.

The parallel processing pipeline 119, as generally presented in FIG. 2 comprises six processing modules and/or computing blocks. These are: 1) optimizing DICOM images 205 for analysis by tuning contrast and brightness window values to improve the precision of aorta detection, 2) aorta detection 207 through constructing bounding boxes on ascending and descending aortic images via ensemble-based deep learning models with both Faster R-CNN and YOLO techniques, 3) iteratively improving window values 211 in the optimization of the aortic imagery through a feed-back loop, 4) performing aortic image segmentation 213 on the aortic images through the U-Net model based on the bounding boxes, 5) creating a 3-dimensional (3D) reconstruction of the aorta and obtaining the centerline of the aorta so as to generate outputs of FIG. 5) measurements of the maximum aorta sizes for ascending and descending sections after angle adjustment based on centerline gradients, and 6) calculating adverse event risk based on aortic maximum size and patient data, using logistic and Cox Proportional Hazard models. These computational blocks are discussed in greater detail next.

In a first computational step in FIG. 2, DICOM images 203 that are inputted to the parallel processing pipeline 119 can be adjusted for two specific characteristics (brightness and contrast) that will enhance the likelihood (e.g., the probability) that actual aortic sections of the image can be identified and isolated. Thus, each input image may undergo a conversion to a Joint Photographic Experts Group (JPEG) image or a Portable Network Graphics (PNG) image prior to follow-on analysis. Once converted into a suitable format, each DICOM image may be rendered within a "window" (typically just an internal rendering for the purpose of image data analysis and not rendered in a traditional display) with the rendered window having an initial brightness setting and an initial contrast setting. The brightness and contrast settings may be adjusted so as to optimize the ability to establish a bounding box around candidate portions that may correspond to an aortic region of interest (e.g., the ascending or descending portions) and for analysis by tuning contrast and brightness window values to improve the precision of aorta detection.

Contrast, as generally used in the industry, is the difference in luminance or color that makes an object (or its representation in an image or display) distinguishable. In digital representation of an image, the contrast is determined by the difference in the color and brightness of one object in comparison to other objects within the same digital rendering. The maximum contrast of a digital image is the contrast ratio or dynamic range and may typically be expressed on a scale from 0 to 100 with 0 being absolute minimum contrast (e.g., every color depicted is the same).

Brightness, as generally used in the industry, is an attribute of visual perception in which a source appears to be radiating or reflecting light. In other words, brightness is the perception elicited by the luminance of a visual image. The perception is not linear to luminance and relies on the context of the viewing environment. Brightness is a subjective sensation of an object being observed and one of the color appearance parameters of many color appearance models, typically denoted as Q. Brightness refers to how much light appears to shine from something and, in the context of a digital image may be represented on a scale of 0 to 100 with 0 being an all-black representation of an image and 100 being all white representation of image.

Thus, in optimizing an image for use in a specific image processing procedure (e.g., Faster R-CNN and YOLO techniques, as discussed below), brightness value and contrast value can be moved up and down on each respective scale from 0-100 to find the optimum settings to isolate imagery of the aorta in each scan. Therefore, in one embodiment, each of these settings may be set at 50 and then the Faster R-CNN and YOLO techniques of the Aorta detection computational block 207 may be undertaken. If a threshold probability is met (discussed further below), then the additional computational steps of bounding and cropping the regions of interest may proceed. However, it is likely that the brightness and contrast may need to be adjusted to try again. Thus, the process may revert back through a feedback loop 211 to update these window values.

These iterative steps may include several different permutations across several embodiments. In a first iterative process, the brightness and contrast values are each incremented by 1 and then the Faster R-CNN and YOLO techniques are attempted again. If there is an improvement in model accuracy, then a next step may be to increment both again until a threshold probability is satisfied. In other embodiments, only one of the two values may be incremented at each iteration. In another embodiment, both values may be decremented if the probability of success is lowered upon each iteration of the Faster R-CNN and YOLO techniques. In still another embodiment, one value may be incremented while the other value is decremented. As success is achieved in optimizing model accuracy, the final setting may be noted and documented as part of a neural network learning algorithm as discussed below with respect to FIGS. 3 and 4. Further, the final values may be persisted to start the next image analysis once the probability threshold of the first image analysis is met. In other embodiments, the values may be reset to a suitable starting point determined to be optimal over time within the trained neural network.

As alluded above, the next step of the computational pipeline 119 may be aorta detection 207 through analysis of the optimized image to construct bounding boxes on ascending and descending aortic sections using one or more image analysis techniques such as Faster R-CNN and YOLO. These analysis techniques are known to those skilled in the art and can identify specific regions of an image along with a probability of being correct (also known as the confidence level). The process may set a threshold for the probability of being correct (e.g., a 70% threshold or a 90% threshold, for example) wherein once this probability threshold is met, the bounded box image is passed along to the next step in the parallel processing pipeline 119 and eventually on to the next image to analyze. Thus, as fresh images are passed to this computational block, a scan of the 2D image of cross-sections of a human thoracic region is conducted.

Figure 6:
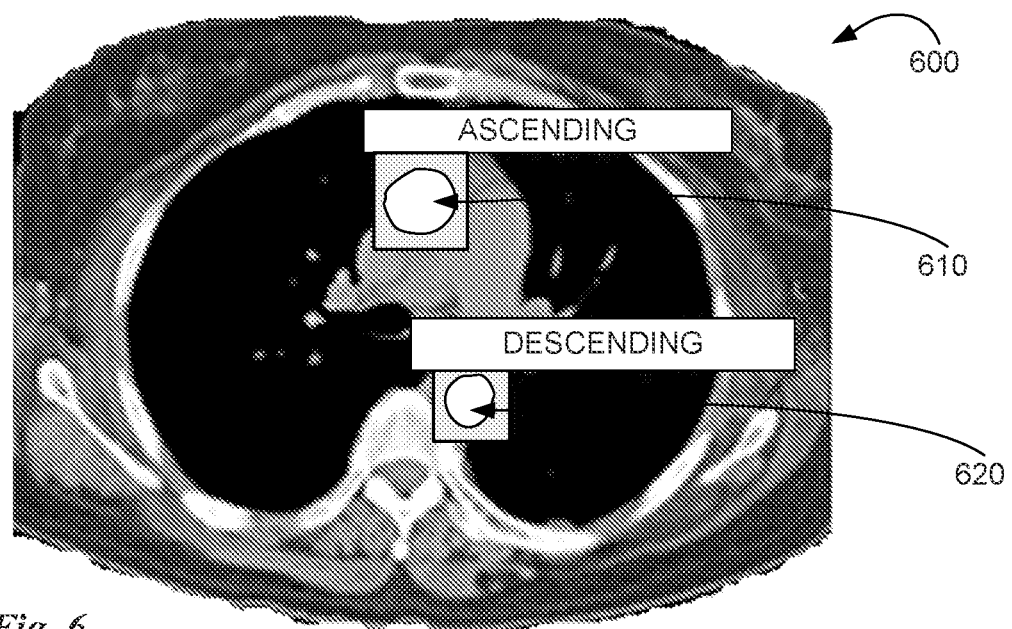
FIGS. 6-10 are images of aortic CT scans used within the systems and methods discussed herein according to embodiments of the subject matter disclosed herein.
Figure 7:
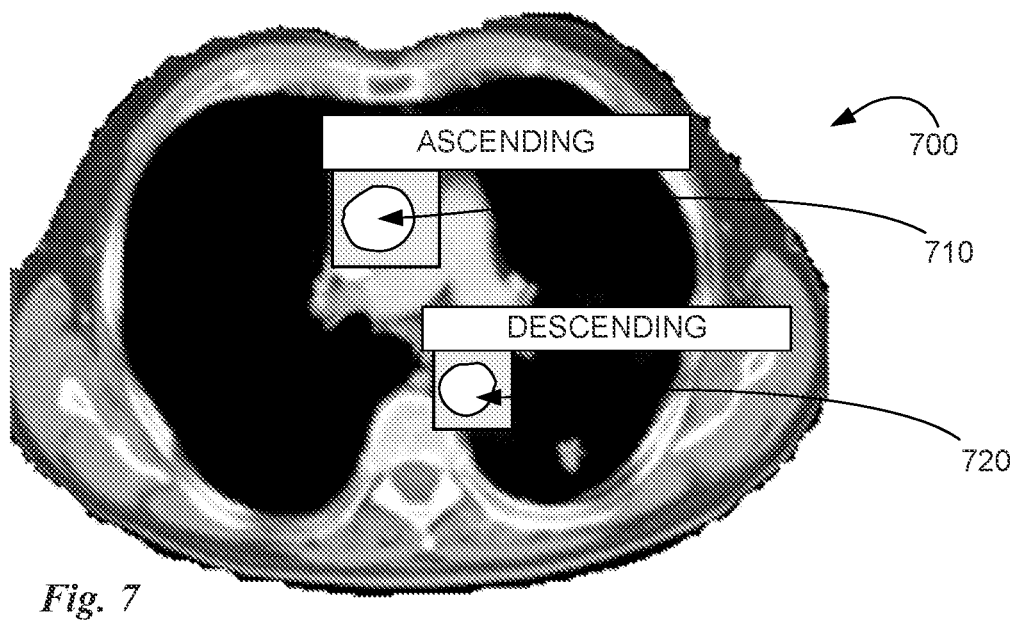

For example, FIG. 6 shows a 2D image 600 of a CT scan converted to a JPEG showing a cross-section of a thoracic region of a human that includes a first region 610 corresponding to an ascending aortic region and a second region 620 corresponding to a descending aortic region. Through an iterative optimization as discussed above, it is revealed that the aortic regions typically exhibit "light colored" areas corresponding to cavities such that one may deduce that generally circular regions correspond to the aorta. Further, in some cross sectional 2D images, both the ascending and descending aortic regions may present with the ascending region typically being larger in area than the descending region. Other regions may exhibit as "light colored" as well, but not generally show a circular region and may be ruled out as likely being an aortic region. By iteratively adjusting brightness and contrast, a probability determination may be used to establish a likelihood of an identified region being an aortic region. Factors that influence this probability include the area covered and the general shape of the area. The total area amongst other similarly situated regions (e.g., other light-colored regions) and location within the overall image (e.g., aortic regions tend to be in the middle of the image). The algorithm may utilize one or more of these factors in establishing a likelihood that the identified region is an aortic region. FIG. 7 shows a resultant enhancement of the image of FIG. 6. that includes a first region 710 corresponding to an ascending aortic region and a second region 720 corresponding to a descending aortic region.

Figure 8:
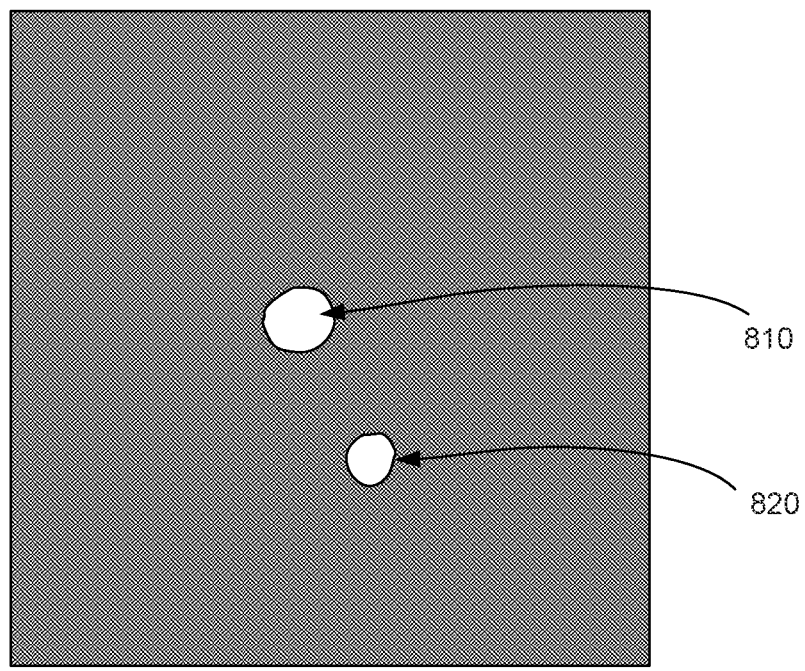

In identifying the region(s), one can see in FIG. 6 and FIG. 7 that a bounding box may be placed around the identified region(s). If the threshold probabilistic determination is met for any given image or regions within an image, then the detection is deemed successful such that the bounding box may become the new bounds of the image to pass along. Thus, as shown in FIG. 8, all other areas outside of the bounding box(es) may be discarded (e.g., data within the image is zeroed out using a U-Net shading technique). Therefore, the only usable data within an initial image is limited to ascending aortic region 810 and the descending aortic region 820.

Figure 9:
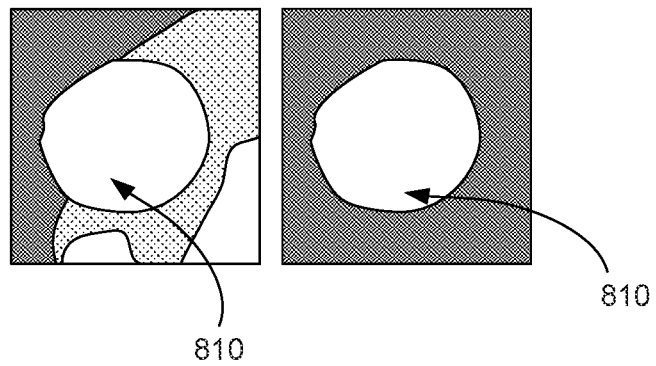
Figure 10:
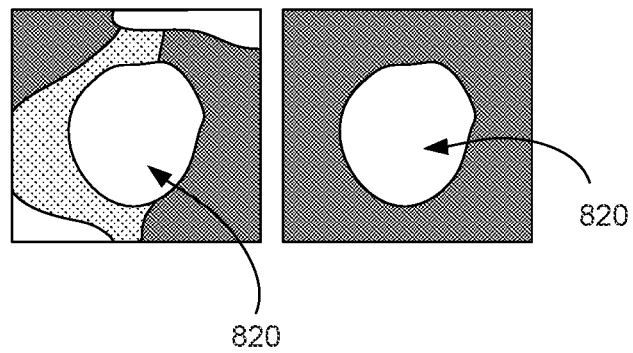

Once shaded, the specific region may be cropped to only be the ascending aortic region 810 (as shown in FIG. 9) or the descending aortic region 820 (as shown in FIG. 10). The bounding box process (as discussed above) may be repeated for each cropped image as well wherein the U-Net shading technique (or other suitable technique) eliminates all superfluous image data beyond the identified, white-colored aortic regions. Thus, one can see that only the aortic regions remain in the second digital image respectively in FIGS. 9-10 (e.g., only the ascending aortic region 810 in FIG. 9 and the descending aortic region 820 in FIG. 10).

As each image is probabilistically determined to be useful (e.g., high probability that that isolated and cropped image is, in fact, the purported bounds of an underlying aortic region of interest in each image), an aortic image segmentation process 213 may be performed on the series of aortic images with high probabilities of containing the underlying aortic region. That is, each newly isolated image of each segment of the aorta may be associated with a z-axis value (e.g., the depth of the 2D image) such that eventually a 3D model of the aorta may be generated from the series of isolated aortic images as optimized through the first several iterations of the process of computational steps described above.

As a contained set of images are optimized and assimilated for a patient as discussed above, the assimilated series of 2D images may be individually analyzed to first determine a centerline point of the processed image at computational block 215. The centerline point, in one embodiment, may be determined by a center-of-mass calculation for each individual processed image. That is, based on a distribution of the image data (in terms of black and white scale) across both the x-axis and the y-axis, there exists a mean value in each dimension that shall serve as the centerline of the image. Utilizing the series of centerline determinations, one may interpolate a 3D image of the aortic regions by aligning the centerline points of each image thereby creating a 3D reconstruction of the aorta. Thus, each successive image has a calculated and determinable center point and by "stacking" each image upon the next at the appropriate depth level, a 3D model of the aortic regions emerges as shown in FIG. 11 which may be one output 222 of the parallel processing pipeline 119.

Figure 11:
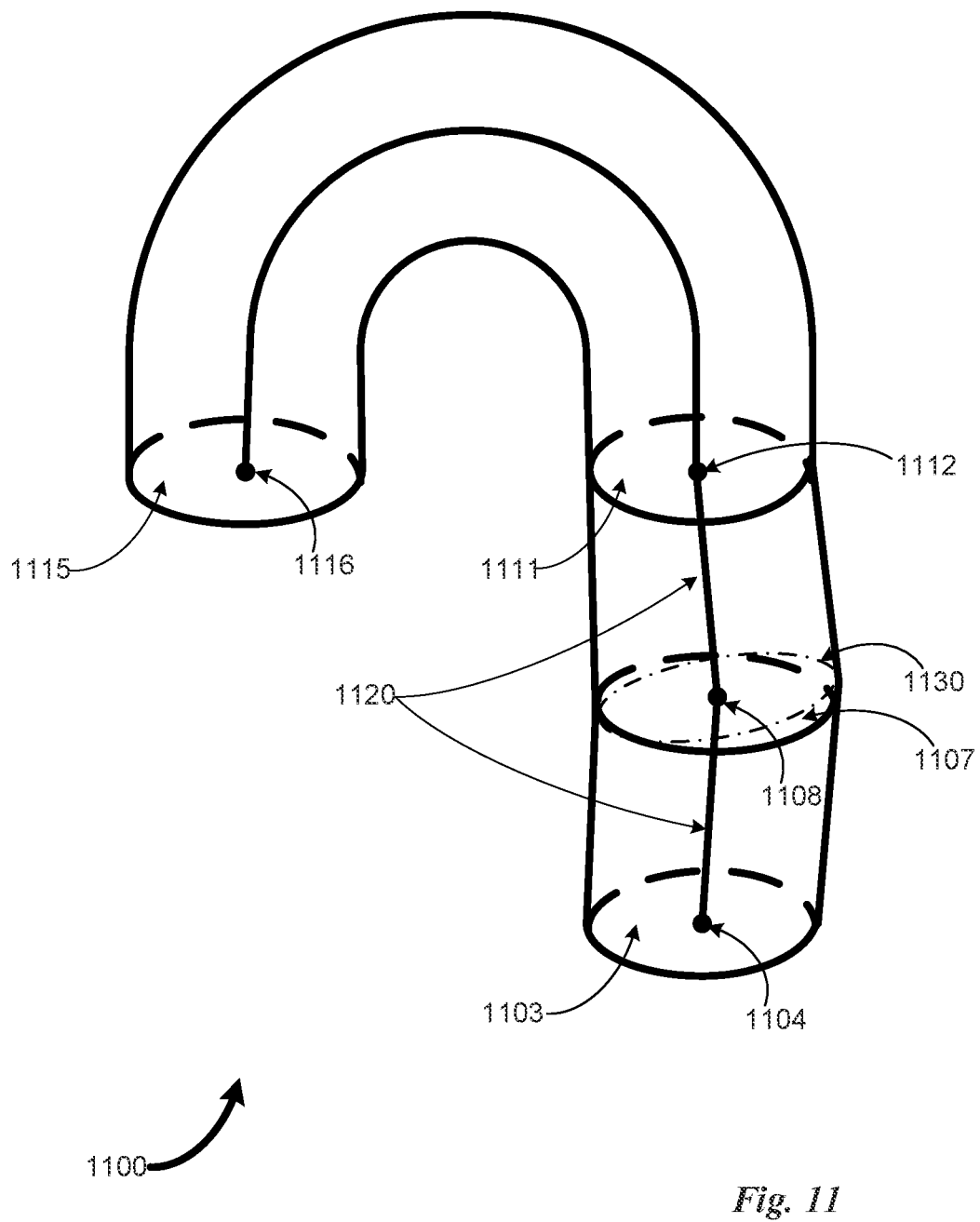
FIG. 11 is a recreated 3D image of aortic CT scans showing each detected center of mass as the center point for each aorta region using spline interpolation on all the center points to arrive at a 3D curve according to an embodiment of the subject matter disclosed herein.

FIG. 11 is a recreated 3D image 1100 of aortic CT scans showing each detected center of mass as the center point for each aorta region using spline interpolation on all the center points to arrive at a 3D curve according to an embodiment of the subject matter disclosed herein. Only four different centerline points are shown in FIG. 11 for ease of illustration, but a skilled artisan understands that many point calculation points may be used in a 3D model reconstruction equivalent to the granularity of the underlying DICOM scans. Thus, a first 2D image scan 1103 may be represented in the 3D model at the lowest depth measurement point wherein this first image corresponds to the descending aortic region and there is no portion of the ascending portion of the aorta that is measured at this depth. This first 2D image 1103 may have a calculated center point 1104.

Continuing this example in FIG. 11, a second 2D image scan 1107 may be represented in the 3D model at the next depth measurement point wherein this second image still corresponds to the descending aortic region and as there remains no portion of the ascending portion of the aorta that is measured at this depth. This second 2D image 1103 may have a calculated center point 1108 yielding a slightly sloped centerline 1120 as the calculated centerline is not in congruence with the first calculated center point 1104. Similarly, a third 2D image scan 1111 may be represented in the 3D model at the next depth measurement point wherein this third image may have two portions wherein one portion 1111 corresponds to the descending aortic region and a second portion 1115 (with its own calculated center point 1116) corresponds of the ascending portion of the aorta that is measured at this depth. For the purposes of calculating the centerline and associated center points, these two images 1111 and 1115 at this depth are treated as separate images. Thus, this third 2D image 1111 may have a calculated center point 1112 again yielding a slightly sloped centerline 1120 as the calculated centerline is not in congruence with the second calculated center point 1104. The slope of the centerline 1120 at this section is different from the slope of the centerline 1120 below.

As each depth is assimilated into the 3D model, one may then calculate the diameter of the modelled aortic regions at each depth. However, to take into account aortic regions that are not completely vertical, one must take into account the slope of the centerline at each measured location and extrapolate a diameter using data from neighboring boundaries of detected aortic regions. Thus, one can see that a plane that is normal to the slope of the centerline near the second 2D image results in an extrapolated image 1130 (shown in a lighter dotted line) that may have a slightly larger diameter than any of the 2D images aligned normal to the scan axis. Overall, referring back to FIG. 2, a second output 220 of the parallel processing pipeline 119 may deliver a maximum aortic diameter given the series of 2D scanned images in the DICOM set.

Shifting focus back to FIG. 2, the two different outputs generated by the parallel processing pipeline 119 may be used in a diagnostics modelling and prediction engine 116. In one embodiment, the diagnostic prediction engine 116 may calculate adverse event risk based on the measured aortic maximum size as well as additional patient medical and demographic data. One such model is the Cox Proportional Hazard model for assessing the data as assembled with respect to a patient DICOM file as well as feeding additional data into a machine learning algorithm to improve both image enhancement (block 205 using feedback from block 211) as well as patient diagnostics to inform future patients with similarly situated data using the Cox Proportional Hazard model (e.g., machine learning that influences the diagnostic). The specific aspects and computational blocks of the machine learning algorithm and neural network the diagnostic modelling and prediction engine 116 are discussed next with respect to FIG. 3 and its subsequent training methodology below with respect to FIG. 4.

Figure 3:
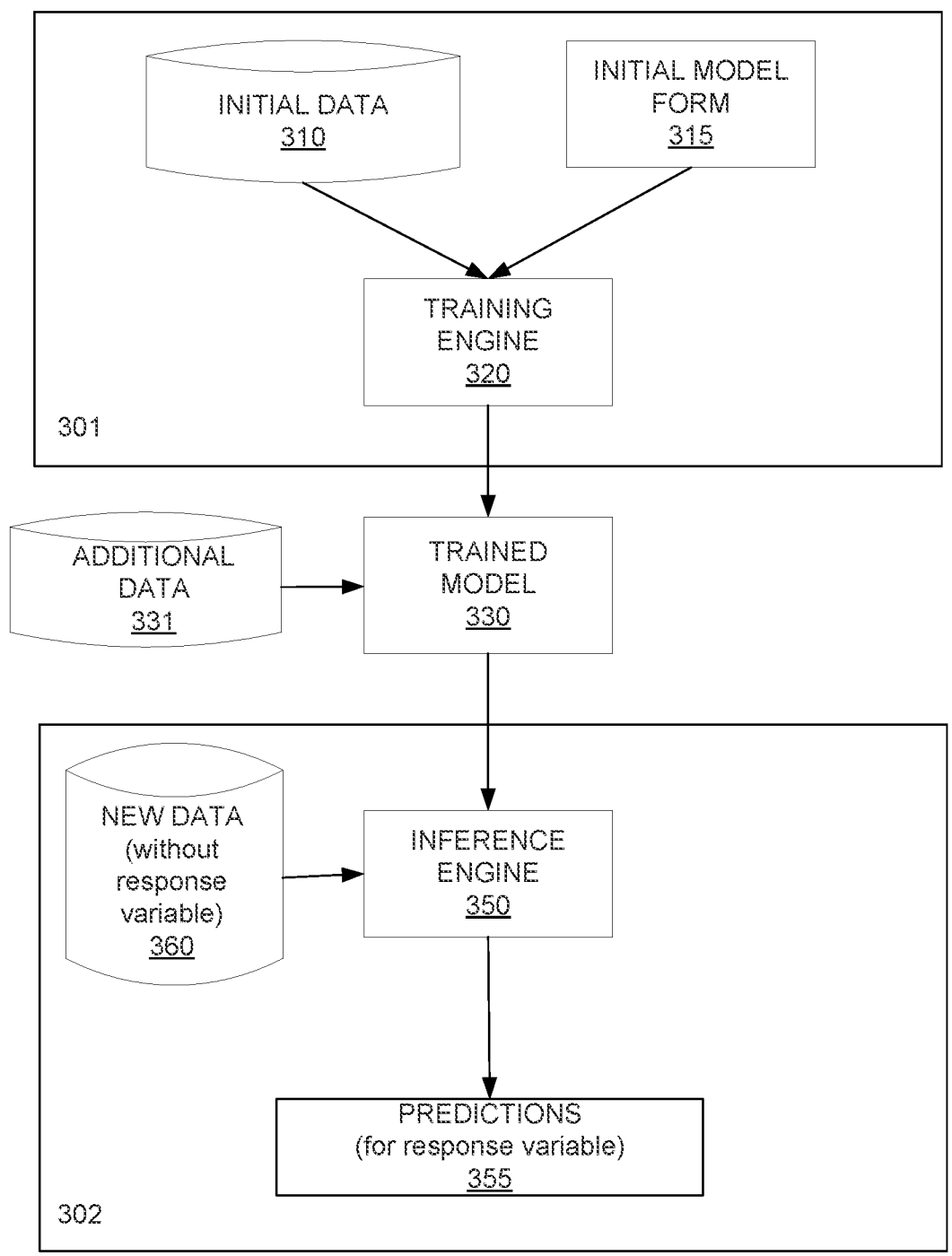
FIG. 3 is a logical block diagram of different aspects of the modelling and prediction engine of FIG. 2 presented in a manner that illustrates the iterative machine learning aspects according to an embodiment of the subject matter disclosed herein.

FIG. 3 is a block diagram 300 of logical block diagram of different aspects of the modelling and prediction engine 116 of FIG. 2 presented in a manner that illustrates the iterative machine learning aspects according to an embodiment of the subject matter disclosed herein. In this block diagram 300, some modules may represent functional activities, such as data collection and training, but this diagram is, nevertheless, presented in a block diagram format to convey the functional aspects of the overall modelling and prediction computing block 116. Thus, in FIG. 3, a first aggregated set of functions includes the upper half 301 of the diagram where a predictive model is first established and trained for use in making predictions. Once the trained model 330 is established, the lower half 302 of the block diagram of FIG. 3 focuses on generating initial predictions to be checked against expected or historical data as well as new predictions based on new data collected. Collectively, the interrelated functional blocks of FIG. 3 may be commonly referred to as a neural network.

In the upper half 301, initial data 310 may be drawn from an established database (e.g., a database of CT scans 142 of FIG. 1) along with an initialized model form 315 (stored within a local memory 114 of FIG. 1) to a training engine 320. The initial data may include actual collected data from historical records of patients. Further, the initial data may be created based on the learned judgment of best management practices. Further, the initial model form may be pre-established using best modeling practices such that the model form includes known influences, such as Cox Proportional Hazard model as discussed above. This initial model form is simply an initial "best guess" by administrators of the aortic aneurysm detection system. As the initial data 310 may also include outcomes and other measurable performance data, a training engine 320 may begin to "train" the model from 315 by identifying specific data correlations and data trends that affect the measurable outcomes from the initial data 315.

With the trained model 330 established, an inference engine 350 may then utilize the trained model 330 along with newly collected input data (e.g., new patient CT scan data and/or DICOM file). Thus, a user may wish to use the system to predict the aortic aneurysm adverse event risk based on a current CT scan and/or DICOM file. The user may present new data 360 in the form of a DICOM file. The new data 360 is used by the inference engine 350 that employs the use of the trained model 330 to generate one or more predictions 355 (e.g., new matches for the user, influencing the listing vector or the user vector, and the like). This additional data 331 may then be used in an iterative manner to further influence the trained model by assimilating relative feedback across several possible weighting factors. Thus, the diagnostic prediction portion may be influenced by resultant data fed back into the system as well as an improvement to the image enhancement iterative process discussed above with respect to FIG. 2.

Figure 4:
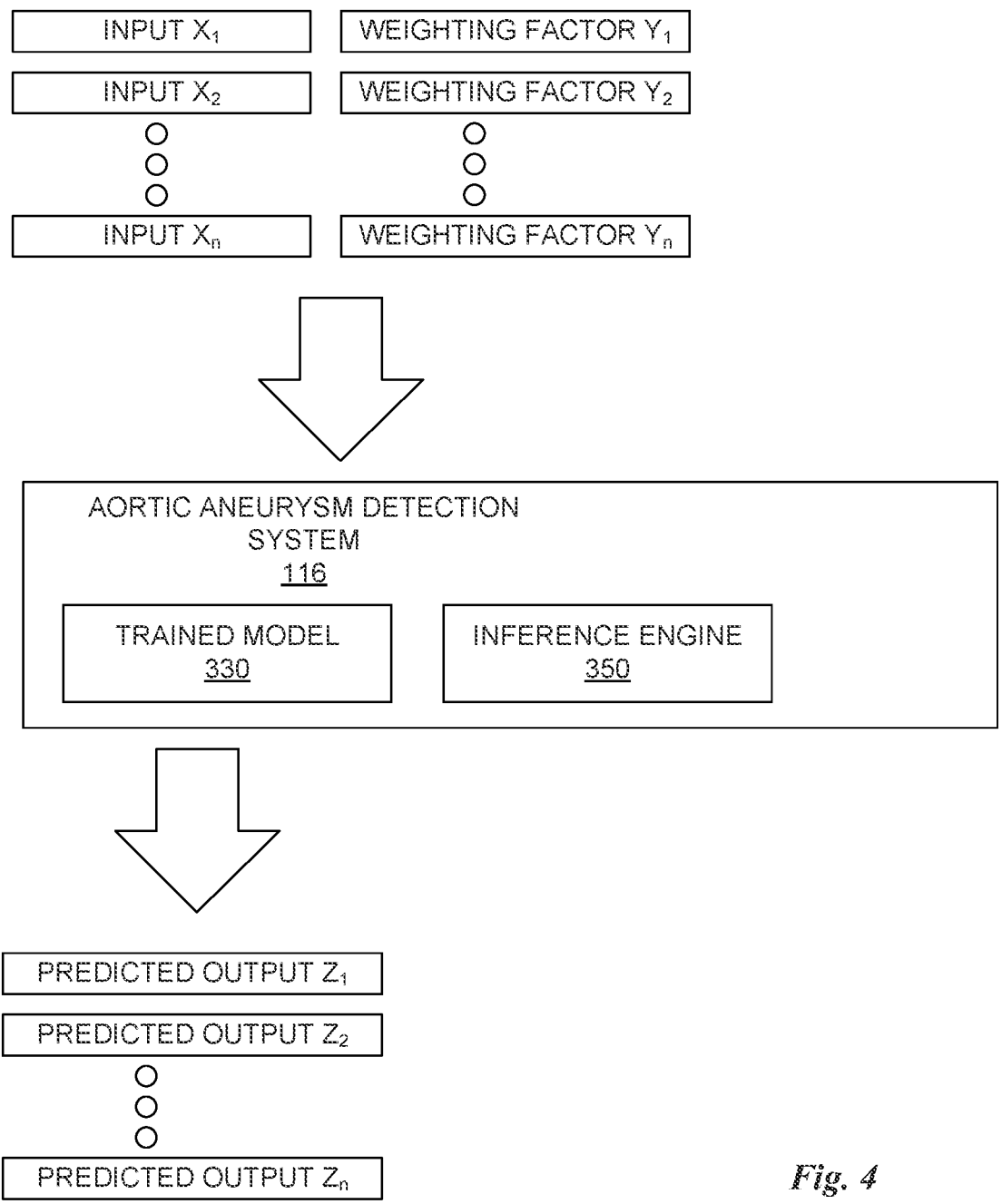
FIG. 4 is a hybrid block diagram and flow chart illustrating inputs, factors, and weighting influences for influencing predicted outcome in a predictive aortic aneurysm detection system of FIG. 1 according to an embodiment of the subject matter disclosed herein.

FIG. 4 is a hybrid block diagram and flow chart illustrating inputs, factors, and weighting influences for generating a predicted outcome in an aortic aneurysm detection system of FIG. 1 according to an embodiment of the subject matter disclosed herein. These influences and weighting factors may improve diagnostic models such as the Cox Proportional Hazard model as discussed above. In general, all inputs that may be used to determine one or more outcomes or predictions are illustrated in a top portion of FIG. 4, while all outcomes and predictions are illustrated in a bottom portion of FIG. 4. FIG. 4 illustrates one or more algorithms that may be realized during the establishment of the trained model 330 whereby the aortic aneurysm detection system 116 may establish specific predictions $Z_1$-$Z_n$ based on new data through its inference engine 350. That is, given inputs $X_1$-$X_n$, each with corresponding weighting factors $Y_1$-$Y_n$, (that may have changing values based on the iterative influence of activity) the inference engine 350 will utilize the trained model 330 to generate predicted outputs $Z_1$-$Z_n$. Generally speaking, the weighting factors $Y_1$-$Y_n$ may be a result of the prediction process whereby different weighting factors are determined to be more or less influential over the prediction processes (such as patient age, weight, ethnicity, family history, and the like). For example, initial weighting factors may be zero as there does not exist any predictive data yet—but as predictions emerge and comparisons to reality are determined, weightings of influential factors may also emerge.

Figure 5:
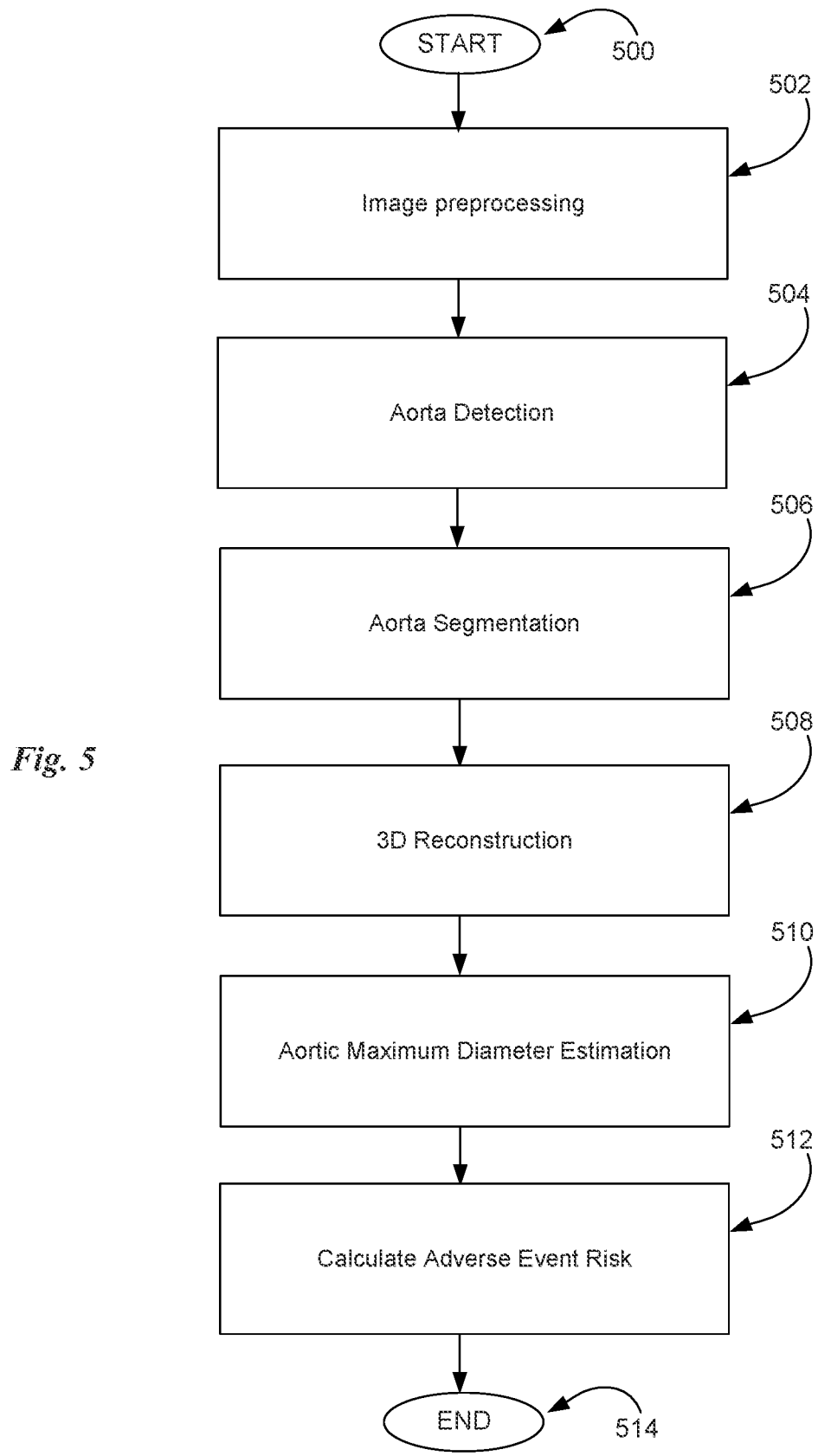
FIG. 5 is a method flow chart illustrating an exemplary computer-based method for establishing a trained neural network and updating the trained neural network to generate aortic aneurysm predictions and detections according to an embodiment of the subject matter disclosed herein.

FIG. 5 is a method flow chart illustrating an exemplary computer-based method for utilizing a trained neural network to generate aortic aneurysm predictions and detections according to an embodiment of the subject matter disclosed herein. The steps shown in this flow chart are illustrative of steps discussed above with respect to the parallel processing pipeline 119 of FIG. 2 and the skilled artisan understands that these steps may be performed in differing orders than what is presented here, and steps may be repeated or omitted as desired. The method may begin at step 500 and proceed to step 502 for image preprocessing. Here, the contrast and brightness (CB) values of the input images needed to achieve the best aorta detection performance are found by initially training the model on a small dataset of DICOM images, but over a range of different CB values, to determine the optimal setting. All images are then preprocessed based on optimized values of contrast and brightness. The inputs are DICOM files, outputs are a series of JPEG files. Such images are represented in FIG. 6 as discussed previously.

The next step 504 comprises Aorta detection. Among the thoracic cross-section CT scans, the ascending and descending aorta area will be marked on each depth level in different colors as the ground truth masks. Based on the output from step 502, one may apply an ensemble-based deep learning models with both Faster R-CNN and YOLO architectures to construct bounding boxes for aorta detection. Given the model prediction and the ground truth, the model performance is evaluated according to two metrics, the intersection over union (IOU) score and the Dice score. Such images are represented in FIG. 7.

The next step 506 is aorta segmentation. Given the images with bounding boxes suggesting the aorta area, one may perform aorta segmentation using the U-Net architecture. Here, the cropped 2D image for each aorta is stored for further processing in steps 510 and 512. In step 510, 3D reconstruction of the aorta and its centerline is achieved as discussed above. Using the stored image data from step 508, we detect the center of mass as the center point for each aorta region and apply spline interpolation on all the center points to get a 3D curve 1100 as depicted in FIG. 11, which will be used as the estimated centerline of the aorta. In step 512, Aorta maximum diameter estimation is achieved. Due to bending and off-axis orientation of the aorta, cross-sections of the aorta captured from CT scans are generally not perpendicular to the centerline; this will result in biased estimation of the maximum diameter of the aorta. Therefore, we use the centerline vector (e.g., centerline slope) from step 510 to achieve unbiased estimates by calculating the diameter along planes that are perpendicular to the centerline vectors. The maximum diameter of the entire aorta as the final output is obtained by comparing the unbiased maximum diameter in each image slice. At step 514, one may calculate adverse event risk based on aortic maximum size and patient data, using logistic and Cox Proportional Hazard models.

Figure 12:
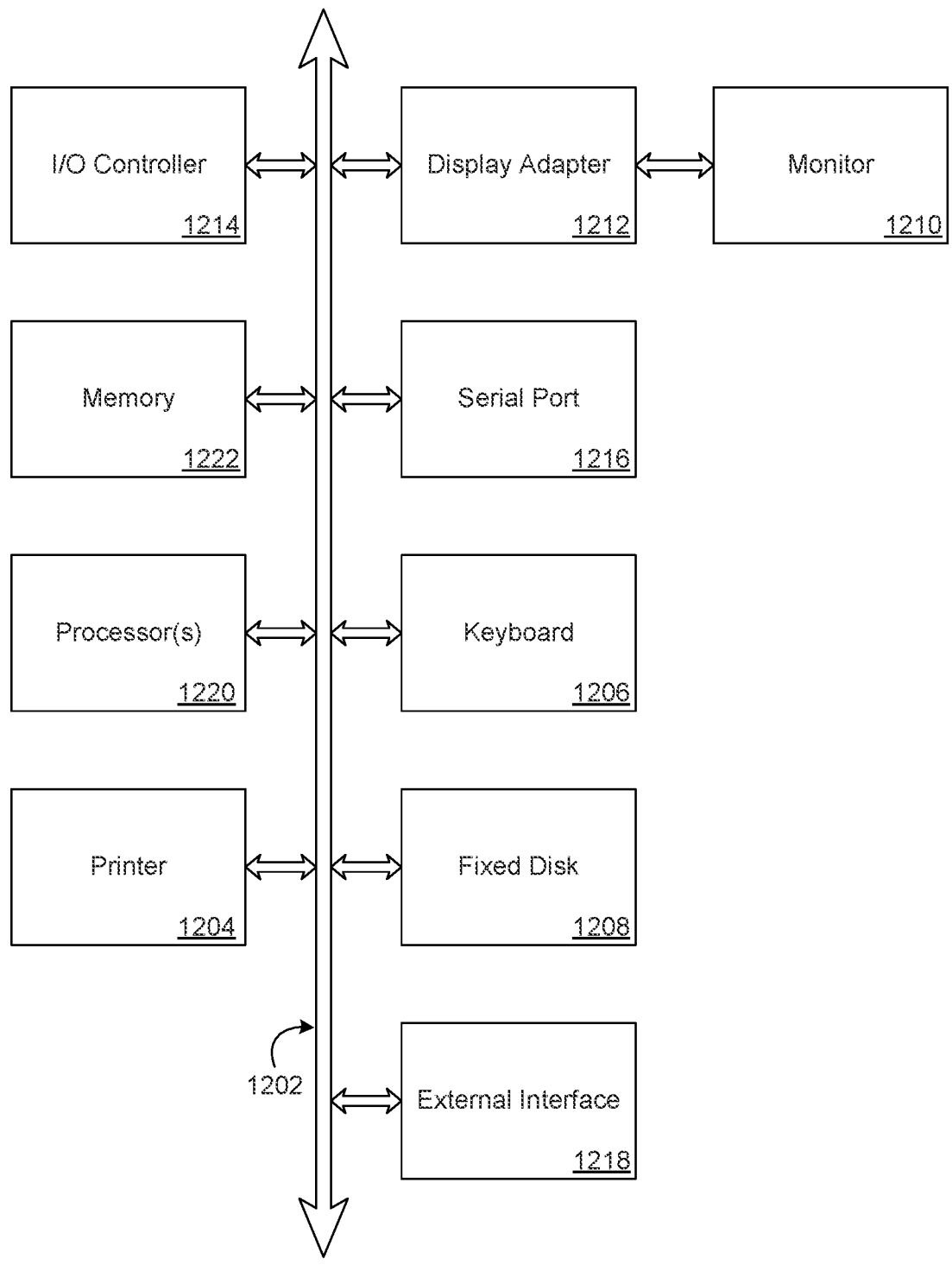
FIG. 12 is a block diagram of a generic computing device for realizing methods leading to aortic aneurysm detection systems and strategies according to one or more embodiments of the subject matter disclosed herein.

FIG. 12 and the following discussion are intended to provide a brief, general description of a suitable computing environment in which the subject matter disclosed herein may be implemented. Although not required, aspects of the subject matter disclosed herein will be described in the general context of computer-executable instructions, such as program modules, being executed by a personal computer. Generally, program modules include routines, programs, objects, components, data structures, and the like, which perform particular tasks or implement particular abstract data types. Such program modules may be embodied in both a transitory and/or a non-transitory computer-readable medium having computer-executable instructions. Moreover, those skilled in the art will appreciate that the invention may be practiced with other computer system configurations, including hand-held devices, cellular or mobile telephones, multiprocessor systems, microprocessor-based or programmable consumer electronics, network PCs, minicomputers, mainframe computers, and the like. The invention may also be practiced in distributed computing environments where tasks are performed by remote processing devices that may be linked through a communications network. In a distributed computing environment, program modules may be located in both local and remote memory storage devices.

FIG. 12 is a diagram illustrating elements or components that may be present in a computer device or system 1200 configured to implement a method, process, function, or operation in accordance with an embodiment of the information disclosed herein. It may include the system, apparatus, methods, processes, functions, and/or operations for enabling efficient configuration and presentation of a user interface to a user, based on the user's previous behavior, and may be wholly or partially implemented in the form of a set of instructions executed by one or more programmed computer processors, such as a central processing unit (CPU), graphics processing unit (GPU), or microprocessor. Such processors may be incorporated in an apparatus, server, client or other computing or data processing device operated by, or in communication with, other components of the system. FIG. 12 illustrates elements or components that may be present in a computer device or system 1200 configured to implement a method, process, function, or operation in accordance with an embodiment. The subsystems shown in FIG. 12 are interconnected via a system bus 1202. Additional subsystems include a printer 1204, a keyboard 1206, a fixed disk 1208, and a monitor 1210, which is coupled to a display adapter 1212. Peripherals and input/output (I/O) devices, which couple to an I/O controller 1214, can be connected to the computer system by any number of means known in the art, such as a serial port 1216. For example, the serial port 1216 or an external interface 1218 can be utilized to connect the computer device 1200 to additional devices and/or systems not shown in FIG. 21, including a wide area network (such as the Internet), a mouse input device, and/or a scanner. The interconnection via the system bus 1202 allows one or more processors 1220 to: communicate with each subsystem, control the execution of instructions that may be stored in a system memory 1222 and/or the fixed disk 1208, and to exchange information between subsystems. The system memory 1222 and/or the fixed disk 1208 may represent any tangible computer-readable medium.

The subject matter described herein can be implemented in software in combination with hardware and/or firmware. For example, the subject matter described herein may be implemented in software executed by one or more processors. In one exemplary implementation, the subject matter described herein may be implemented using a non-transitory computer-readable medium having stored thereon computer executable instructions that when executed by the processor of a computer control the computer to perform steps. Exemplary computer-readable media suitable for implementing the subject matter described herein include non-transitory computer-readable media, such as disk memory devices, chip memory devices, programmable logic devices, and application-specific integrated circuits. In addition, a computer-readable medium that implements the subject matter described herein may be located on a single device or computing platform or may be distributed across multiple devices or computing platforms.

The system may use a bus 1202 that can be any of several types of suitable bus structure(s) including the memory bus or memory controller, a peripheral bus or external bus, and/or a local bus using any suitable variety of available bus architectures including, but not limited to, 11-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Universal Serial Bus (USB), Advanced Graphics Port (AGP), Personal Computer Memory Card International Association bus (PCMCIA), and Small Computer Systems Interface (SCSI).

The systems and methods herein enable rapid ingestion of big data sets in a distributed computing environment. The metadata-driven approach intake processing reduces source ingestion time, enhances reliability, and automates data intake. Furthermore, the platform agnostic nature of the present disclosure can operate on an input source in any electronic format. The error logging and reporting of the present disclosure further enable users to monitor progress and identify bad data based on predetermined or dynamically generated validation tolerances.

As used herein, "match" or "associated with" or similar phrases may include an identical match, a partial match, meeting certain criteria, matching a subset of data, a correlation, satisfying certain criteria, some correspondence, an association, an algorithmic relationship and/or the like. Similarly, as used herein, "authenticate" or similar terms may include an exact authentication, a partial authentication, authenticating a subset of data, some correspondence, satisfying certain criteria, an association, an algorithmic relationship and/or the like.

Any communication, transmission and/or channel discussed herein may include any system or method for delivering content (e.g., data, information, metadata, and the like), and/or the content itself. The content may be presented in any form or medium, and in various embodiments, the content may be delivered electronically and/or capable of being presented electronically. For example, a channel may comprise a website or device (e.g., Facebook, YOUTUBE®, APPLE®TV®, PANDORA®, XBOX®, SONY®PLAYSTATION®), a uniform resource locator ("URL"), a document (e.g., a MICROSOFT® Word® document, a MICROSOFT® Excel® document, an ADOBE®.pdf document, and the like), an "eBook," an "emagazine," an application or microapplication (as described herein), an SMS or other type of text message, an email, Facebook, Twitter, MMS and/or other type of communication technology. In various embodiments, a channel may be hosted or provided by a data partner. In various embodiments, the distribution channel may comprise at least one of a merchant website, a social media website, affiliate or partner websites, an external vendor, a mobile device communication, social media network and/or location-based service. Distribution channels may include at least one of a merchant website, a social media site, affiliate or partner websites, an external vendor, and a mobile device communication. Examples of social media sites include FACEBOOK®, FOURSQUARE®, TWITTER®, MYSPACE®, LINKEDIN®, and the like. Examples of affiliate or partner websites include AMERICAN EXPRESS®, GROUPON®, LIVINGSOCIAL®, and the like. Moreover, examples of mobile device communications include texting, email, and mobile applications for smartphones.

In various embodiments, the methods described herein are implemented using the various particular machines described herein. The methods described herein may be implemented using the below particular machines, and those hereinafter developed, in any suitable combination, as would be appreciated immediately by one skilled in the art. Further, as is unambiguous from this disclosure, the methods described herein may result in various transformations of certain articles.

For the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include client data; merchant data; financial institution data; and/or like data useful in the operation of the system. As those skilled in the art will appreciate, user computer may include an operating system (e.g., WINDOWS® NT®, WINDOWS®95/98/2000®, WINDOWS®XP®, WINDOWS® Vista®, WINDOWS® 7®, OS2, UNIX®, LINUX®, SOLARIS®, MacOS, and the like) as well as various conventional support software and drivers typically associated with computers.

The present system or any part(s) or function(s) thereof may be implemented using hardware, software, or a combination thereof and may be implemented in one or more computer systems or other processing systems. However, the manipulations performed by embodiments were often referred to in terms, such as matching or selecting, which are commonly associated with mental operations performed by a human operator. No such capability of a human operator is necessary, or desirable in most cases, in any of the operations described herein. Rather, the operations may be machine operations. Useful machines for performing the various embodiments include general purpose digital computers or similar devices.

In fact, in various embodiments, the embodiments are directed toward one or more computer systems capable of carrying out the functionality described herein. The computer system includes one or more processors, such as a central processing unit (CPU). The processor is connected to a communication infrastructure (e.g., a communications bus, cross-over bar, or network). Various software embodiments are described in terms of this exemplary computer system. After reading this description, it will become apparent to a person skilled in the relevant art(s) how to implement various embodiments using other computer systems and/or architectures. Computer system can include a display interface that forwards graphics, text, and other data from the communication infrastructure (or from a frame buffer not shown) for display on a display unit.

Computer system also includes a main memory, such as for example random access memory (RAM) and may also include a secondary memory. The secondary memory may include, for example, a hard disk drive and/or a removable storage drive, representing a floppy disk drive, a magnetic tape drive, an optical disk drive, etc. The removable storage drive reads from and/or writes to a removable storage unit in a well-known manner. Removable storage unit represents a floppy disk, magnetic tape, optical disk, etc., which is read by and written to by the removable storage drive. As will be appreciated, the removable storage unit includes a computer-usable storage medium having stored therein computer software and/or data.

In various embodiments, secondary memory may include other similar devices for allowing computer programs or other instructions to be loaded into computer system. Such devices may include, for example, a removable storage unit and an interface. Examples of such may include a program cartridge and cartridge interface (such as that found in video game devices), a removable memory chip (such as an erasable programmable read only memory (EPROM), or programmable read only memory (PROM)) and associated socket, and other removable storage units and interfaces, which allow software and data to be transferred from the removable storage unit to computer system.

Computer system may also include a communications interface. Communications interface allows software and data to be transferred between computer system and external devices. Examples of communications interface may include a modem, a network interface (such as an Ethernet account), a communications port, a Personal Computer Memory Account International Association (PCMCIA) slot and account, etc. Software and data transferred via communications interface are in the form of signals which may be electronic, electromagnetic, optical, or other signals capable of being received by communications interface. These signals are provided to communications interface via a communications path (e.g., channel). This channel carries signals and may be implemented using wire, cable, fiber optics, a telephone line, a cellular 30 link, a radio frequency (RF) link, wireless and other communications channels.

The terms "computer program medium" and "computer-usable medium" and "computer-readable medium" are used to generally refer to media such as removable storage drive and a hard disk installed in hard disk drive. These computer program products provide software to computer system.

Computer programs (also referred to as computer control logic) are stored in main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

In various embodiments, software may be stored in a computer program product and loaded into computer system using removable storage drive, hard disk drive or communications interface. The control logic (software), when executed by the processor, causes the processor to perform the functions of various embodiments as described herein. In various embodiments, hardware may include components such as application-specific integrated circuits (ASICs). Implementation of the hardware state machine so as to perform the functions described herein will be apparent to persons skilled in the relevant art(s).

The various system components may be independently, separately or collectively suitably coupled to the network via data links which includes, for example, a connection to an Internet Service Provider (ISP) over the local loop as is typically used in connection with standard modem communication, cable modem, Dish Networks®, ISDN, Digital Subscriber Line (DSL), or various wireless communication methods, see, e.g., GILBERT HELD, UNDERSTANDING DATA COMMUNICATIONS (1996), which is hereby incorporated by reference. It is noted that the network may be implemented as other types of networks, such as an interactive television (ITV) network. Moreover, the system contemplates the use, sale or distribution of any goods, services or information over any network having similar functionality described herein.

Any databases discussed herein may include relational, hierarchical, graphical, or object-oriented structure and/or any other database configurations. Common database products that may be used to implement the databases include DB2 by IBM® (Armonk, N.Y.), various database products available from ORACLE® Corporation (Redwood Shores, Calif.), MICROSOFT® Access® or MICROSOFT® SQL Server® by MICROSOFT® Corporation (Redmond, Wash.), MySQL by MySQL AB (Uppsala, Sweden), or any other suitable database product. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks. Additionally, aspects of system described herein may utilize frameworks and technologies such as NET Core, Xamarin, WPF/XAML, ADO.NET, Entity Framework, React, Next, FLASK, MS SQL, Mongo DB, Azure, AWS.

One skilled in the art will also appreciate that, for security reasons, any databases, systems, devices, servers, or other components of the system may consist of any combination thereof at a single location or at multiple locations, wherein each database or system includes any of various suitable security features, such as firewalls, access codes, encryption, decryption, compression, decompression, and/or the like.

The computers discussed herein may provide a suitable website or other Internet-based graphical user interface which is accessible by users. In one embodiment, the MICROSOFT® INTERNET INFORMATION SERVICES® (IIS), MICROSOFT® Transaction Server (MTS), and MICROSOFT® SQL Server, are used in conjunction with the MICROSOFT® operating system, MICROSOFT® NT web server software, a MICROSOFT® SQL Server database system, and a MICROSOFT® Commerce Server. Additionally, components such as Access or MICROSOFT® SQL Server, ORACLE®, Sybase, Informix, MySQL, Interbase, and the like, may be used to provide an Active Data Object (ADO) compliant database management system. In one embodiment, the Apache web server is used in conjunction with a Linux operating system, a MySQL database, and the Per, PHP, and/or Python programming languages.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, JAVA® APPLE®, JAVASCRIPT, active server pages (ASP) common gateway interface scripts (CGI), extensible markup language (XML), dynamic HTML, cascading style sheets (CSS), AJAX (Asynchronous JAVASCRIPT and XML), helper applications, plug-ins, and the like. A server may include a web service that receives a request from a web server, the request including a URL and an IP address (123.56.555.234). The web server retrieves the appropriate web pages and sends the data or applications for the web pages to the IP address. Web services are applications that are capable of interacting with other applications over a communication means, such as the internet. Web services are typically based on standards or protocols such as XML, SOAP, AJAX, WSDL and UDDI. Web services methods are well known in the art and are covered in many standard texts. See, e.g., ALEX NGHIEM, IT WEB SERVICES: A ROADMAP FOR THE ENTERPRISE (2003), hereby incorporated by reference.

Middleware may include any hardware and/or software suitably configured to facilitate communications and/or process transactions between disparate computing systems. Middleware components are commercially available and known in the art. Middleware may be implemented through commercially available hardware and/or software, through custom hardware and/or software components, or through a combination thereof. Middleware may reside in a variety of configurations and may exist as a standalone system or may be a software component residing on an Internet server. Middleware may be configured to process transactions between the various components of an application server and any number of internal or external systems for any of the purposes disclosed herein. WEBSPHERE MQ™ (formerly MQSeries) by IBM®, Inc. (Armonk, N.Y.) is an example of a commercially available middleware product. An Enterprise Service Bus ("ESB") application is another example of middleware.

The system and method may be described herein in terms of functional block components, screen shots, optional selections, and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as R, C, C++, C#, JAVA®, JAVASCRIPT, VBScript, Macromedia Cold Fusion, COBOL, MICROSOFT® Active Server Pages, assembly, PERL, PHP, awk, Python, Visual Basic, SQL Stored Procedures, PL/SQL, any UNIX shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JAVASCRIPT, VBScript or the like. For a basic introduction of cryptography and network security, see any of the following references: (1) "Applied Cryptography: Protocols, Algorithms, And Source Code In C," by Bruce Schneier, published by John Wiley & Sons (second edition, 1995); (2) "JAVA® Cryptography" by Jonathan Knudson, published by O'Reilly & Associates (1998); (3) "Cryptography & Network Security: Principles & Practice" by William Stallings, published by Prentice Hall; all of which are hereby incorporated by reference.

As will be appreciated by one of ordinary skill in the art, the system may be embodied as a customization of an existing system, an add-on product, a processing apparatus executing upgraded software, a standalone system, a distributed system, a method, a data processing system, a device for data processing, and/or a computer program product. Accordingly, any portion of the system or a module may take the form of a processing apparatus executing code, an Internet-based embodiment, an entirely hardware embodiment, or an embodiment combining aspects of the Internet, software, and hardware. Furthermore, the system may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

The system and method are described herein with reference to screen shots, block diagrams and flowchart illustrations of methods, apparatus (e.g., systems), and computer program products according to various embodiments. It will be understood that each functional block of the block diagrams and the flowchart illustrations, and combinations of functional blocks in the block diagrams and flowchart illustrations, respectively, can be implemented by computer program instructions.

These computer program instructions may be loaded onto a general-purpose computer, special-purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special-purpose hardware-based computer systems which perform the specified functions or steps, or suitable combinations of special-purpose hardware and computer instructions. Further, illustrations of process flow and the descriptions thereof may make reference to use WINDOWS®, webpages, websites, web forms, prompts, and the like. Practitioners will appreciate that the illustrated steps described herein may comprise in any number of configurations including the use of WINDOWS®, webpages, web forms, popup WINDOWS®, prompts and the like. It should be further appreciated that the multiple steps as illustrated and described may be combined into single webpages and/or WINDOWS® but have been expanded for the sake of simplicity. In other cases, steps illustrated and described as single process steps may be separated into multiple webpages and/or WINDOWS® but have been combined for simplicity. Further yet, all aspects of any computer system mentioned heretofore may utilize known Machine Learning and AI Technologies such as Tensorflow, Keras, (CNN, RNN), SpaCy, NeuroNER, NER, FastText, Scikit-learn, OpenCV, XGBoost, LightGBM, Pandas, Scipy, Numpy, Matplotlib, Seaborn, RAS.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

Systems, methods, and computer program products are provided. In the detailed description herein, references to "various embodiments", "one embodiment", "an embodiment", "an example embodiment", and the like, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Although the disclosure includes a method, it is contemplated that it may be embodied as computer program instructions on a tangible computer-readable carrier, such as a magnetic or optical memory or a magnetic or optical disk. All structural, chemical, and functional equivalents to the elements of the above-described exemplary embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims.

Furthermore, no element, component, or method step in the present disclosure is intended to be dedicated to the public regardless of whether the element, component, or method step is explicitly recited in the claims. No claim element herein is to be construed under the provisions of 35 U.S.C. 112 (f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What has been described above includes examples of aspects of the claimed subject matter. It is, of course, not possible to describe every conceivable combination of components or methodologies for purposes of describing the claimed subject matter, but one of ordinary skill in the art may recognize that many further combinations and permutations of the disclosed subject matter are possible. Accordingly, the disclosed subject matter is intended to embrace all such alterations, modifications and variations that fall within the spirit and scope of the appended claims. Furthermore, to the extent that the terms "includes," "has" or "having" are used in either the detailed description or the claims, such terms are intended to be inclusive in a manner similar to the term "comprising" as "comprising" is interpreted when employed as a transitional word in a claim.

Since many modifications, variations, and changes in detail can be made to the described preferred embodiments of the subject matter, it is intended that all matters in the foregoing description and shown in the accompanying drawings be interpreted as illustrative and not in a limiting sense. Thus, the scope of the subject matter should be determined by the appended claims and their legal equivalence.

What is claimed is:

1. A computer-implemented method for detecting aortic aneurysms, comprising:

receiving a series of images associated with a thoracic region of a patient, the series of images comprising scans of at least one aortic region;

iteratively enhancing each image in the series of images to detect and isolate images of respective aortic regions;

for each enhanced image, determining a center of mass point in an x-y plane corresponding to portions of each image corresponding to an aortic region;

constructing a centerline of an aorta portion in response to determining the center of mass for each successive image;

extrapolating a series of aorta diameters based on a vector of the centerline for each of the series of images aligned according to the center of mass point calculations; and generating a communication to a diagnostic engine that identifies the maximum extrapolated aorta dimension.

2. The computer-implemented method of claim 1, wherein iteratively enhancing each image in the series of images further comprises:

assessing an unenhanced image to determine a probability that an aortic region is isolated in the image;

in response to determining that the probability does not meet or exceed a threshold probability, applying a YOLO object detection technique to the image to enhance portions of the image by adapting bright and contrast values;

reassessing the enhanced image to determine a second probability that an aortic region is isolated in the image;

in response to determining that the second probability does not meet or exceed the threshold probability, applying a second YOLO object detection technique to the image to enhance portions of the image by adapting bright and contrast values;

reassessing the enhanced image to determine a third probability that an aortic region is isolated in the image; and in response to determining that the third probability does meet or exceed the threshold probability, applying a bounding box to the image to eliminate image data that is not determined to be an aortic region.

3. The computer-implemented method of claim 1, wherein iteratively enhancing each image in the series of images further comprises:

assessing an unenhanced image to determine a probability that an aortic region is isolated in the image;

in response to determining that the probability does not meet or exceed a threshold probability, applying a Faster R-CNN object detection technique to the image to enhance portions of the image by adapting bright and contrast values;

reassessing the enhanced image to determine a second probability that an aortic region is isolated in the image;

in response to determining that the second probability does not meet or exceed the threshold probability, applying a second Faster R-CNN object detection technique to the image to enhance portions of the image by adapting bright and contrast values;

reassessing the enhanced image to determine a third probability that an aortic region is isolated in the image; and in response to determining that the third probability does meet or exceed the threshold probability, applying a bounding box to the image to eliminate image data that is not determined to be an aortic region.

4. The computer-implemented method of claim 1, wherein iteratively enhancing each image in the series of images further comprises:
- assessing an unenhanced image to determine a probability that an aortic region is isolated in the image;
- in response to determining that the probability does not meet or exceed a threshold probability, applying a Faster R-CNN object detection technique to the image to enhance portions of the image by adapting bright and contrast values;
- reassessing the enhanced image to determine a second probability that an aortic region is isolated in the image;
- in response to determining that the second probability does not meet or exceed the threshold probability, applying a YOLO object detection technique to the image to enhance portions of the image by adapting bright and contrast values;
- reassessing the enhanced image to determine a third probability that an aortic region is isolated in the image; and
- in response to determining that the third probability does meet or exceed the threshold probability, applying a bounding box to the image to eliminate image data that is not determined to be an aortic region.

5. The computer-implemented method of claim 1, wherein iteratively enhancing each image in the series of images further comprises applying a U-Net shading technique to each image to isolate portions of each image identified as an aortic region.

6. The computer-implemented method of claim 1, further comprising:
- constructing a 3D model of an aorta in response to determining the centerline; and
- displaying the constructed 3D model on a display.

7. The computer-implemented method of claim 1, further comprising:
- generating a probability of an adverse event using the diagnostic prediction engine from an adverse event diagnostic model in response to the determined maximum aortic size; and
- influencing the diagnostic model using data generated from the series of enhanced images.

8. The computer-implemented method of claim 1, wherein the aortic region identified comprises an ascending aortic region.

9. The computer-implemented method of claim 1, wherein the aortic region identified comprises a descending aortic region.

10. A computer system for detecting aortic aneurysms, comprising:
- a means for receiving a series of images associated with a thoracic region of a patient, the series of images comprising scans of at least one aortic region;
- a means for iteratively enhancing each image in the series of images to detect and isolate images of respective aortic regions;
- for each enhanced image, a means for determining a center of mass point in an x-y plane corresponding to portions of each image corresponding to an aortic region;
- a means for constructing a centerline of an aorta portion in response to determining the center of mass for each successive image;
- a means for extrapolating a series of aorta diameters based on a vector of the centerline for each of the series of images aligned according to the center of mass point calculations; and
- a means for generating a communication to a diagnostic engine that identifies the maximum extrapolated aorta dimension.

11. The computer system of claim 10, wherein the means for iteratively enhancing each image in the series of images further comprises:
- a means for assessing an unenhanced image to determine a probability that an aortic region is isolated in the image;
- in response to determining that the probability does not meet or exceed a threshold probability, a means for applying a YOLO object detection technique to the image to enhance portions of the image by adapting bright and contrast values;
- a means for reassessing the enhanced image to determine a second probability that an aortic region is isolated in the image;
- in response to determining that the second probability does not meet or exceed the threshold probability, a means for applying a second YOLO object detection technique to the image to enhance portions of the image by adapting bright and contrast values;
- a means for reassessing the enhanced image to determine a third probability that an aortic region is isolated in the image; and
- in response to determining that the third probability does meet or exceed the threshold probability, a means for applying a bounding box to the image to eliminate image data that is not determined to be an aortic region.

12. The computer system of claim 10, wherein the means for iteratively enhancing each image in the series of images further comprises:
- a means for assessing an unenhanced image to determine a probability that an aortic region is isolated in the image;
- in response to determining that the probability does not meet or exceed a threshold probability, a means for applying a Faster R-CNN object detection technique to the image to enhance portions of the image by adapting bright and contrast values;
- a means for reassessing the enhanced image to determine a second probability that an aortic region is isolated in the image;
- in response to determining that the second probability does not meet or exceed the threshold probability, a means for applying a second Faster R-CNN object detection technique to the image to enhance portions of the image by adapting bright and contrast values;
- a means for reassessing the enhanced image to determine a third probability that an aortic region is isolated in the image; and
- in response to determining that the third probability does meet or exceed the threshold probability, a means for applying a bounding box to the image to eliminate image data that is not determined to be an aortic region.

13. The computer system of claim 10, wherein the means for iteratively enhancing each image in the series of images further comprises:
- a means for assessing an unenhanced image to determine a probability that an aortic region is isolated in the image;
- in response to determining that the probability does not meet or exceed a threshold probability, a means for applying a Faster R-CNN objection detection technique to the image to enhance portions of the image by adapting bright and contrast values;

a means for reassessing the enhanced image to determine a second probability that an aortic region is isolated in the image;

in response to determining that the second probability does not meet or exceed the threshold probability, a means for applying a YOLO object detection technique to the image to enhance portions of the image by adapting bright and contrast values;

a means for reassessing the enhanced image to determine a third probability that an aortic region is isolated in the image; and in response to determining that the third probability does meet or exceed the threshold probability, a means for applying a bounding box to the image to eliminate image data that is not determined to be an aortic region.

14. The computer system of claim 10, wherein the means for iteratively enhancing each image in the series of images further comprises a means for applying a U-Net shading technique to each image to isolate portions of each image identified as an aortic region.

15. The computer system of claim 10, further comprising:
a means for constructing a 3D model of an aorta in response to determining the centerline; and
a means for displaying the constructed 3D model on a display.

16. The computer system of claim 10, further comprising:
a means for generating a probability of an adverse event using the diagnostic prediction engine from an adverse event diagnostic model in response to the determined maximum aortic size; and
a means for influencing the diagnostic model using data generated from the series of enhanced images.

17. The computer system of claim 10, wherein the aortic region identified comprises a descending aortic region.

18. A computer-implemented method for training a neural network to detect aortic aneurysms, comprising:
collecting a first data set corresponding to aortic images of multiple patients that are stored in an aortic image database;
collecting a second data set from one or more remote computer users about aortic diagnostics of one or more patients associated with the one or more remote computer users that are exclusive of the first data set;
creating a first training set comprising the collected first data set;
training the neural network in a first stage using the first training set;
applying one or more transformations to the second data set;
creating a second training set for a second stage of training by altering the first training set with data from the second data set; and
altering the neural network in a second stage using the second training set.

19. The computer-implemented method of claim 18, wherein the applying one or more transformations to the second data set comprises applying a YOLO object detection technique to alter one or more images in the second data set.

20. The computer-implemented method of claim 18, wherein the applying one or more transformations to the second data set comprises applying a Faster R-CNN object detection technique to alter one or more images in the second data set.

* * * * *